United States Patent [19]

Auer

[11] Patent Number: 4,487,320
[45] Date of Patent: Dec. 11, 1984

[54] METHOD OF AND APPARATUS FOR DETECTING CHANGE IN THE BREAKOFF POINT IN A DROPLET GENERATION SYSTEM

[75] Inventor: Robert E. Auer, Miami, Fla.

[73] Assignee: Coulter Corporation, Hialeah, Fla.

[21] Appl. No.: 203,121

[22] Filed: Nov. 3, 1980

[51] Int. Cl.³ .............................................. B07C 5/342
[52] U.S. Cl. .................................... 209/3.1; 209/579;
209/906; 346/75; 356/39; 356/72; 361/226;
364/413
[58] Field of Search ................................. 209/3.1–3.3,
209/44.1, 44.2, 546, 548, 549, 571, 579, 906, 127
R; 250/222 R, 222 PC; 356/39, 72, 73, 335, 338;
361/226; 364/413; 346/75

[56] References Cited

U.S. PATENT DOCUMENTS

| | | | |
|---|---|---|---|
| 3,380,584 | 4/1968 | Fulwyler | 209/3 |
| 3,710,933 | 1/1973 | Fulwyler et al. | 209/3.1 |
| 3,761,941 | 9/1973 | Robertson | 346/75 X |
| 3,826,364 | 7/1974 | Bonner et al. | 209/579 X |
| 3,963,606 | 6/1976 | Hogg | 209/3 |
| 4,038,556 | 7/1977 | Auer et al. | 356/73 X |
| 4,047,183 | 9/1977 | Taub | 346/75 X |
| 4,317,520 | 3/1982 | Lombardo et al. | 209/3.1 |
| 4,318,480 | 3/1982 | Lombardo et al. | 209/3.1 |
| 4,318,482 | 3/1982 | Barry et al. | 209/3.1 |
| 4,318,483 | 3/1982 | Lombardo et al. | 364/413 X |
| 4,325,483 | 4/1982 | Lombardo et al. | 209/3.1 |
| 4,347,935 | 9/1982 | Merrill | 209/579 X |

OTHER PUBLICATIONS

H. R. Hulett et al., "Development and Application of a Rapid Cell Sorter" from Clinical Chemistry, vol. 19, No. 8, 1973, pp. 813–816.

Paul K. Horan and Leon L. Wheeless, Jr., "Quantitative Single Cell Analysis and Sorting" from Science, vol. 198, pp. 149–157, Oct. 14, 1977.

Primary Examiner—Robert B. Reeves
Assistant Examiner—Edward M. Wacyra
Attorney, Agent, or Firm—Stephen A. Roen; Gerald R. Hibnick

[57] ABSTRACT

A particle separator for sorting particles suspended in a liquid according to certain characteristics, including a method of and apparatus for detecting a change in the droplet breakoff point of a liquid jet stream which is subjected to vibrations. The vibrations produce amplitude undulations on the surface of the jet stream. The amplitude of the undulations is monitored or interrogated at a fixed point on the jet stream prior to the breakoff point. A change in amplitude of the undulations at that fixed point produces a signal voltage the value of which is proportional to the amplitude change. This signal voltage may be used (1) to alert the operator that a change has occurred in the point at which the jet stream is breaking up into droplets, (2) to automatically control the intensity of the vibrations for restoring the amplitude of undulation at that fixed point to its original state, or (3) to automatically disable the sorting portion of the apparatus. Any one or any combination of the foregoing three happenings can be utilized.

20 Claims, 8 Drawing Figures

METHOD OF AND APPARATUS FOR DETECTING CHANGE IN THE BREAKOFF POINT IN A DROPLET GENERATION SYSTEM

This invention relates to apparatus for sorting minute particles in a fluid, and in particular to such apparatus wherein a liquid jet stream containing these particles is vibrated to produce undulations on the surface of the jet stream and subsequent break-up of the stream into droplets which are then sorted according to the particle characteristics and collected downstream.

BACKGROUND OF THE INVENTION

Apparatus of the foregoing kind may be referred to as flow cytometric sorting systems and are used in the medical researach and diagnostic field for the rapid analysis of blood cells and other biological cells. Systems for cell separation and sorting are described in U.S. Pat. Nos. 4,038,556; 3,963,606; 3,710,933 and 3,380,584, in Science, Vol. 198, pages 149-157, published Oct. 14, 1977, and in the references cited therein.

U.S. Pat. No. 4,038,556 discloses a method of and apparatus for the simultaneous optical measurement of several characteristics of each particle of a group of small particles while the particles are suspended in a liquid.

U.S. Pat. No. 3,963,606 discloses a particle separator for separating particles in a liquid according to certain characteristics including a device for adjusting an electrical delay to be equal to the time between the emergence of a particle from a jet forming aperture to the breakoff point.

U.S. Pat. No. 3,710,933 discloses an apparatus for automatically analyzing and sorting minute particles suspended in a liquid on the basis of certain preselected characteristics.

U.S. Pat. No. 3,380,584 discloses a particle separator in which electrical pulses cause an acoustic coupler driver to vibrate the fluid which contains the particles.

The Science Article, Vol. 198, pages 149-157 discloses a flow cytometer. Fluorescence from biological cells within a fluid stream is measured at the intersection with a laser beam. Droplets containing cell of interest are sorted out of the fluid stream.

To the extent that it might be necessary to understand fully the techniques involved and the teachings of the invention herein, the above patents are incorporated herein for reference.

A major problem in using the cell sorter systems wherein a jet stream subjected to vibrations breaks off into droplets is ascertaining if a change has occurred in the point at which the jet stream is breaking into droplets. If the precise instant of breakoff with relation to the sense point changes, then the instrument ceases to be a cell sorter and becomes a water or saline solution sorter of unknown cell content. An even worse undesired result is that the unwanted particles are sorted when there is such a change in the breakoff point. Such a change is often due to changes in the mechanical coupling coefficients, such as air bubbles entering the flow chamber and partial plugs of the jet stream exit orifice. Optical sensitivies, such as the presence of undesired light, render impractical the use of an illuminating strobe source to observe the breakoff point on the jet stream while the system is taking data or sorting the cells. It is at this time of sorting that a monitor is most needed.

OBJECTS OF THE INVENTION

An object of the present invention is to sense in a droplet generation system a change in the amplitude of the undulations at a fixed point on the surface of a liquid suspension jet stream prior to the droplet breakoff point, and to indicate that such a change has occurred.

Another object is to automatically disable the sorting function in a particle analyzer and sorting system when there is a significant change in the droplet breakoff point.

A further object is to utilize the information derived from a change in the amplitude of undulation at a fixed point on the surface of a jet stream to restore the level of the amplitude of undulation at that fixed point to its original state.

Other objects will appear from a reading of the detailed description of the invention.

SUMMARY OF THE INVENTION

The liquid jet stream containing the minute particles in suspension is driven at the frequency at which it is desired to generate droplets, normally 20 to 40 KC depending on the diameter of the jet exit orifice; for example, 32 KC frequency for a 76 micron jet exit orifice diameter and 40 KC frequency for a 50-60 micron jet exit orifice diameter. The jet is vibrated by introducing a small disturbance, as from a driven piezo-electric crystal, at the exit orifice of the jet stream. This disturbance is in the form of an undulation or a standing wave on the surface of the jet stream and this undulation grows as the jet advances and causes the breakoff of droplets downstream. The amplitude of the disturbance or undulation at any point along the jet stream is a function of the distance of that point from the point of droplet breakoff and this aspect is described in the report of Richard G. Sweet, SEL-64-004, March 1964, of the Stanford Laboratories of the Stanford University. According to the invention, the amplitude of the undulation at a fixed point is monitored. A change in this amplitude at that fixed point indicates a change in the breakoff point. A laser beam, used as the illumination source in the optical cell sorting systems described in the foregoing U.S. patents, is utilized as a concentrated source of light rays in the monitoring scheme of the invention. The laser beam strikes the jet stream at a fixed point and then the laser beam scatters to provide a lobe pattern of light that is in the same plane as the laser beam and is perpendicular to the jet stream. As is well known, this scattered laser light is modulated by the surface undulations on the jet. Heretofore, this modulation has been considered to be an undesirable phenomenon when cell light scatter is being measured and has usually been blocked out in the instrument. The present invention detects such modulation by positioning a photo diode in the plane of laser light scatter. The output of the photo diode is converted to a voltage which may be used (1) to alert the operator either visually or audibly that a change has occurred in the point at which the jet stream is breaking up into droplets, (2) to automatically control the intensity of the vibrations applied to the jet for restoring the amplitude of undulation at the point on the jet at which it is being monitored, or (3) to automatically disable the apparatus. Any one or any combination of the foregoing happenings can be utilized in the practice of the invention.

If desired, a secondary source of concentrated light rays other than the laser beam can be used to impinge on or interrogate the jet stream at a point closer to the droplet breakoff point where the undulations are larger and, therefore, where the signal obtained therefrom is larger. In this case the photo diode would be judiciously positioned to receive the light scattered or reflected from the jet.

A feature of the invention is the sorting disabling circuitry which includes a fast change detector responsive to a rectified output whose D.C. level is proportional to the percentage modulation of the beam of concentrated light rays (laser beam, for example) as affected by the undulations on the surface of the jet stream. This detector controls a relay driver latching mechanism which acts to disable the sorting function of the particle analyzer whenever there is a significant change in the amplitude of undulation on the jet stream. This circuitry is provided with an operator reset device and an alarm which, if desired, can indicate the type of change based on the polarity of the output from the fast change detector.

Another feature is an automatic gain control (AGC) loop system for varying the intensity of the vibrations applied by the piezo-electric crystal to the jet stream, for slow changes in the amplitude of modulation. The foregoing-mentioned rectified output serves as a control voltage for the AGC loop. This loop system varies the power which is applied to drive the piezo-electric crystal. As a result, fine, as distinguished from course, amplitude corrections on the surface of the jet stream is obtainable. An arm-disable control for the AGC system enables initial setting of the droplet breakoff point.

BRIEF DESCRIPTION OF THE DRAWINGS

Throughout the figures of the drawings the same parts are designated by the same reference numerals.

DESCRIPTION OF PREFERRED EMBODIMENT

Figure 1:
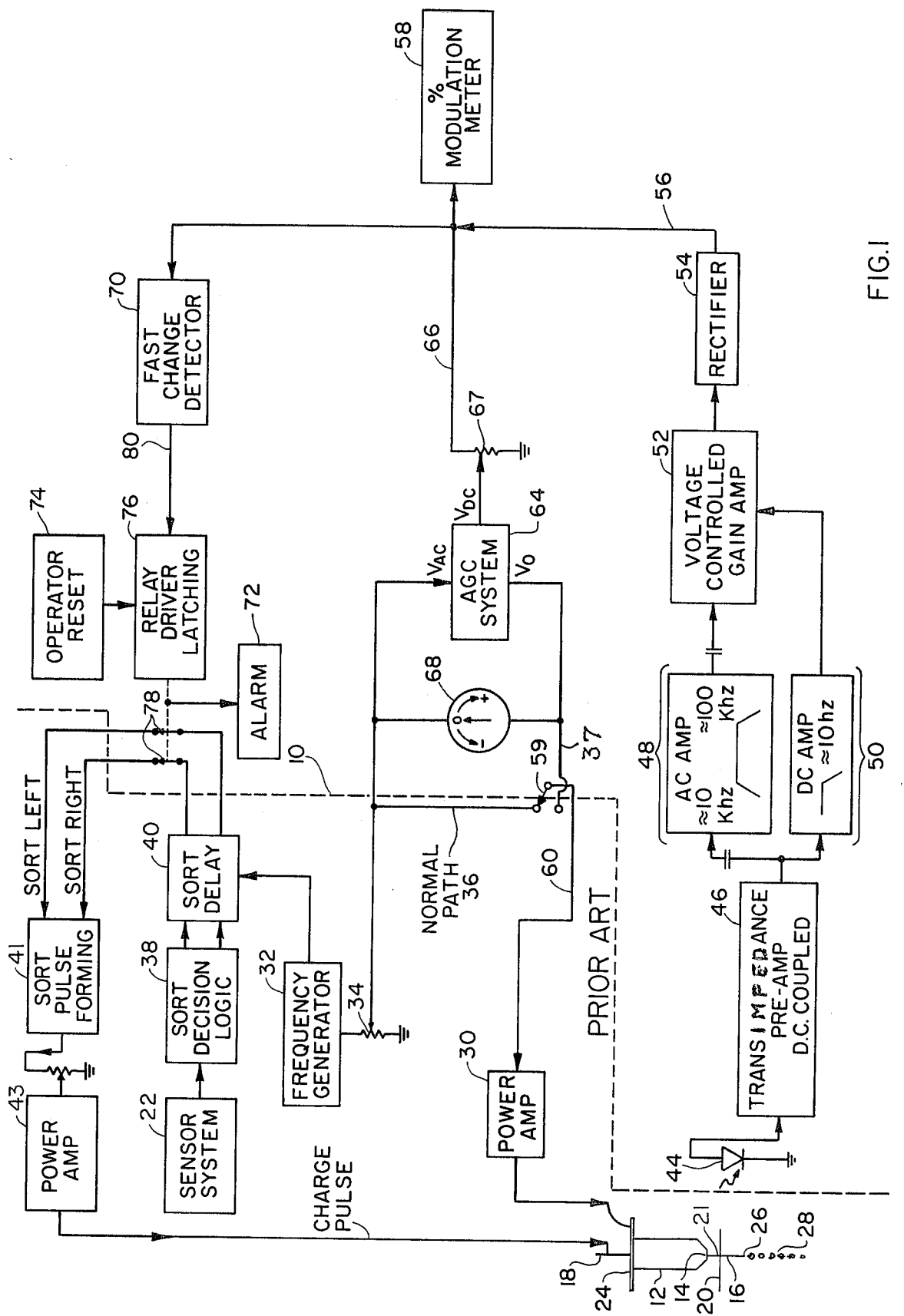
FIG. 1 is a block diagram showing how the electrical elements of the invention are coupled to a known type of particle analyzer and sorter.

The block diagram of FIG. 1 is divided into two parts by a dot-dash line 10. System components to the left of the dot-dash line are those which normally exist in a known type particle analyzer and sorting system, sometimes referred to as a flow cytometric sorting system. One such known sorting system is found in the TPS and EPICS series of instruments manufactured and sold by Coulter Electronics, Inc. of Hialeah, Fla. 33010. Only those components of the particle analyzer and sorter have been shown which are necessary to explain the operation of the present invention. System components to the right of the dot-dash line 10 comprise parts of the present invention which have been added and couple to the known particle analyzer and sorter for achieving the objects of the invention. It should be noted that the automatic gain control (AGC) feature and the disabling feature involving a relay driver latching mechanism of the invention are inserted at two locations into the normal signal paths of the particle analyzer and sorting system as will appear in more detail hereinafter.

The known particle analyzer and sorting system shown to the left of the dot-dash line 10 will now be briefly described. It includes a flow chamber 12 into which a saline solution (normally 13 p.s.i.g.) is introduced under pressure and exits through a small orifice 14 (diameter ranges from 50μ to 200μ, depending upon the application of the system) to form a liquid jet stream 16. The sample (a suspension of minute particles, such as blood cells or biological cells) is introduced into the flow chamber 12 through a tube 18. Below the exit orifice 14 and above and prior to the breakoff pair the jet stream 16 is interrogated by a light source or radiation means 20 (normally a laser beam) and the response of the minute particle in the sample to the illumination (normally light scatter and fluorescence) is detected by the sensor system 22 also at a point prior to and above the breakoff point.

The flow chamber 12 is mounted to and supported by a piezo-electric crystal assemblage 24 which vibrates the chamber 12 at a high frequency. The exact frequency at which the chamber 12 vibrates is dependent on the selected diameter of the exit orifice 14 which frequency is normally 20–40 KC. These vibrations impart small disturbances, normally undulations, on the surface of the jet 16 which grow, due to well known surface tension effects, and eventually pinch the jet off at a breakoff point 26 into well defined droplets 28. The exact distance from the nozzle containing the orifice 14 to the breakoff point 26 is inversely proportional to the amplitude or the initial disturbance of undulation. The size of the disturbance is proportional to the amplitude of the signal voltage applied to the crystal 24, if the mechanical coupling coefficients of the system hold constant. Unfortunately, there are several factors which can cause changes in the mechanical coupling coefficients and these factors are difficult to eliminate. These include air bubbles entering the flow chamber 12 with the sample or with the saline solution and partial plugs of the exit orifice 14 due to debris, such as broken-up cells or fat.

The piezo-electric crystal is driven by a power amplifier 30 which normally derives its signal from a frequency generator 32 through a variable potentiometer 34 which is used to vary the amplitude of the signal applied to crystal 24 and therefore vary the nominal breakoff point 26. Potentiometer 34 serves as a coarse correction source to the drive of power amplifier 30 driving the crystal 24. Line 36 designates the normal path from the potentiometer 34 to the power amplifier in the absence of the components of the present invention. The system of the present invention has incorporated a switch 59 which is not present in the prior art systems, for a purpose described hereinafter.

Connected to the sensor 22 is the sort decision logic 38 in which the signals obtained from the detectors (not shown but forming part of the sensor system 22) are applied to a set of criteria to decide whether or not it is desired to capture the particle originating those signals. If capture is desired, that decision must be delayed, as by sort delay 40, while the particle travels from the sense point to the breakoff point. A sort pulse is then formed by sort pulse forming circuit 41 and amplified and applied, through power amplifier 43, to the jet stream as a voltage just as the droplets which will contain the desired particle breaks off from the jet. Because of this impressed voltage the droplets break off with a net charge. The jet of droplets passes through an intense constant electric field which accelerates the charged droplets in the horizontal plane as they travel downwards. Thus charged droplets travel in a different path from the path uncharged droplets and fall into different capture vessels, thereby effecting a physical sorting of the particles. A typical rate of sorting for this process is 4,000 particles per second. Reference is made to U.S. Pat. No. 3,380,584 which discloses a way of impressing a voltage on a downstream portion of the jet stream containing particles to be charged for subsequent collection, and to an article by Hulett, Bonner, Sweet & Herzenberg, CLINICAL CHEMISTRY, Vol. 19, No. 8, 1973, which discloses impressing a voltage on an upstream portion of the jet stream for the same purpose.

The foregoing system is known in the art and no claim is made herein to this prior art method of analyzing and sorting minute particles. Such apparatus is disclosed in the aforementioned U.S. patents and the references cited therein.

The present invention makes use of the relationship between the amplitude of undulation on the surface of the jet stream at any fixed point and the position of the droplet breakoff point to ascertain that there has been a change in the droplet breakoff point. As stated hereinabove, the amplitude of the undulations increases as the breakoff point is approached. An increase in amplitude of undulation at any given point along the jet is an indication that the breakoff point is closer while a decrease in the amplitude is an indication that the breakoff point is further away. The apparatus of the present invention monitors the position of the breakoff point to effect any one of the following three results: (1) to provide an indication, either visually, as by means of a meter, or audibly, by means of an alarm, of a change in the breakoff point, (2) to disable the sorting process and sound an alarm if there is a fast change in the breakoff point, or (3) to automatically and promptly restore the breakoff point, as by means of an automatic gain control loop, for small and slow changes in the breakoff point.

The system components to the right of the dot-dash line 10 of the block diagram of FIG. 1 comprise parts of the present invention which couple to the known particle analyzer and sorter appearing at the left of dot-dash line 10, and include a photo diode or sensing means 44 which detects the light scattered by the jet stream 16 as a result of the impact thereon by the concentrated beam of intense light 20. This scattered light has two components: a D.C. component which is proportional to the size of the jet stream 16 and the power of the light beam 20 (the laser, for example); and an A.C. component which is proportional to the undulations on the jet stream 16 at the sense point 21, the point on the jet stream 16 at which the beam of light strikes it, and the power of the intense light beam 20 (the laser). The diode 44 is operated in the current mode, that is to say it is terminated in low impedance, thereby producing a linear optical power-to-current relationship and reducing the effects of diode capacitance for maximum electronic bandwidth. Photo diode 44 is coupled to an operational amplifier 46 which is operated as a transimpedance amplifier. Amplifier 46 converts the current from the diode 44 to a voltage linearly. The output from the transimpedance amplifier 46 splits into an A.C. path including A.C. amplifier 48 and a D.C. path including D.C. amplifier 50.

The A.C. path 48 contains the basic information to be used in the practice of the invention, viz, the amplitude of the undulations on the jet stream. Because the amplitude of the undulation signals generated at the photo diode detector 44 are low, this signal is given considerable gain by the A.C. amplifier 48, of the order of $10^3$. In order to improve the signal-to-noise ratio in this A.C. path the bandwidth of the A.C. amplifiers is limited to the range of frequencies of oscillation applied to the piezo-electric crystal 24.

Since the size of the jet stream 16 is held constant during a test run of sample particles and is rarely changed, and the D.C. component is proportional to the size of the jet stream 16 and the power of the laser 20, then a change in the D.C. level in the path including D.C. amplifier 50 can be considered to be a change in laser power. The signal through the D.C. path controls the gain of a voltage controlled gain amplifier 52 in the output of the A.C. path, thereby enabling the A.C. path signal to be normalized as to laser power, as a result of which recaliberation of the apparatus is eliminated each time the power of the laser 20 is changed. Stated another way, the D.C. path removes the effect of a change in laser power from the measurement of the distance from the sensing point 21 to the breakoff point 26.

Figure 8:
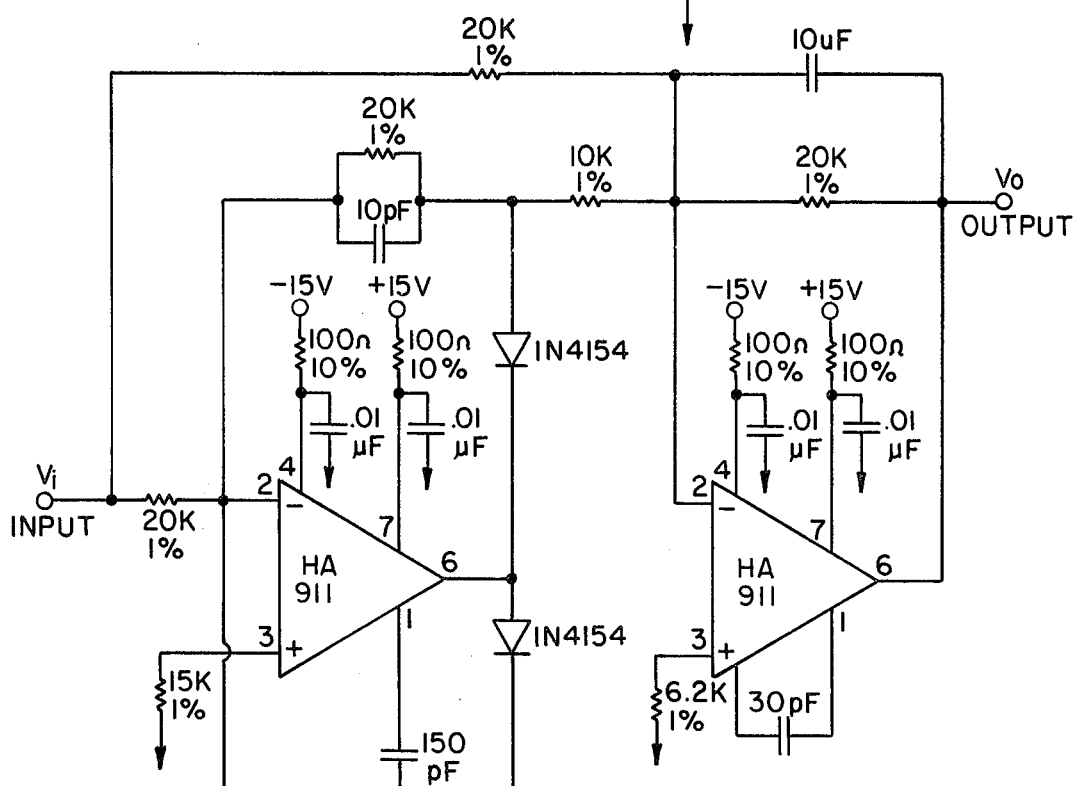

The A.C. signal from the voltage-controlled amplifier 52 is rectified by rectifier 54 (preferably a full-wave rectifier to obtain a smoother D.C. signal output therefrom) to provide a D.C. signal on lead 56 which is proportional to the amplitude of the undulations on the jet stream 16, and proportional to the distance from the sense point 21 to the breakoff point 26. The details of one suitable full wave rectifier which can be used is shown in FIG. 8.

The invention discloses three ways for utilizing the D.C. voltage on lead 56. The simplest is to drive a percentage modulation meter 58 which provides a visual indication as to the position of the droplet breakoff point 26 on the jet stream 16. Properly calibrated, such a meter 58 can be used to set the breakoff point 26 by manually adjusting potentiometer 34 and using the normal path 36 in the known analyzer and sorter apparatus to bypass the AGC system hereinafter described. The meter 58 is connected so as to be operable at all times.

Figure 7:
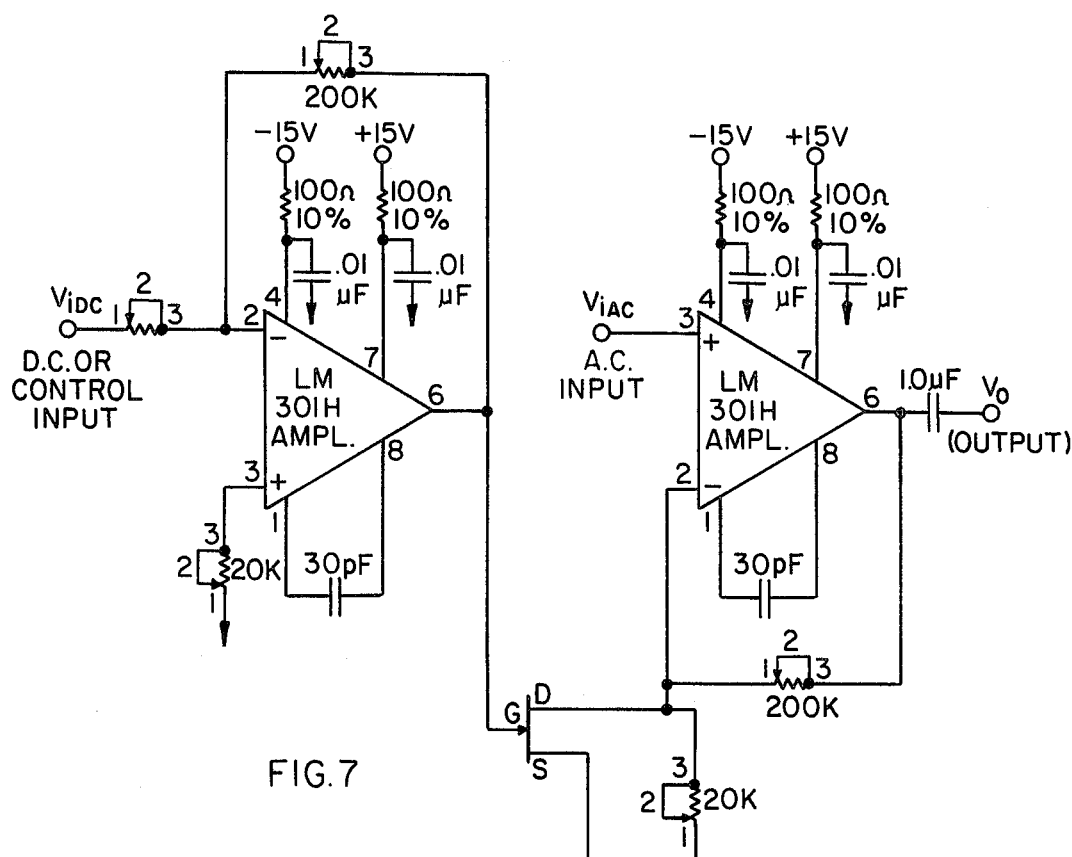

The rectified voltage on lead 56 (the output from rectifier 54) can also be used as a control voltage in an automatic gain control (AGC) loop which will provide fine, as distinguished from coarse, corrections to the voltage drive or power amplifier 30 which feeds the piezo-electric crystal transducer 24 over path 60, and therefore fine corrections in the drift in the breakoff point 26, assuming, of course, that control of the normal path 36 is transferred by switching means 59 when the AGC feature of the invention is utilized. This AGC loop includes an AGC amplifier system 64 which is fed from the voltage on lead 56 over lead 66, and is similar in design to the circuitry of voltage controlled gain amplifier 52 as illustrated in FIG. 7. A suitable double pole-single throw switch 59 is connected across leads 36 and 37. Switch 59 serves to effectively deactivate the AGC loop from the system when it is desired to initially set up the analyzer and sorter for a specific droplet delay. After the proper time delay has been set, the AGC system 64 is armed or activated to maintain the desired breakoff point. Prior to activation of the AGC, the voltage output terminal Vo (lead 37) is adjusted to the same amplitude as that on the normal path 36, by means of potentiometer 67 as is indicated by the null detection meter 68, after which switch 59 can be thrown to transfer control of the power amplifier 30 to the AGC system.

Another way of monitoring the breakoff point 26 on the jet 16 is by means of a system including a fast change detector 70 to which the rectified voltage on lead 56 is fed. The output 80 of fast change detector 70 is zero if a D.C. signal is being applied (which is the case when the breakoff point 26 is constant) and changes from zero if a "fast" change in droplet breakoff point is encountered. The polarity of the change in the output 80 of fast change detector 70 indicates whether the rectified signal level from rectifier 54 has increased or decreased. The output from detector 70 can drive an alarm circuit 72 to alert the operator of a change in the breakoff point. This same output can also drive a relay system composed of a driver latching mechanism 76, which, in turn, serves to automatically disable the sorting system, via leads 78 in the particle analyzer and sorter. Operator reset 74 serves to manually reset the driver latching mechanism 76. The alarm 72 can be made to indicate the type of change in the breakoff point based on the polarity of the output from the detector 70.

Figure 2:
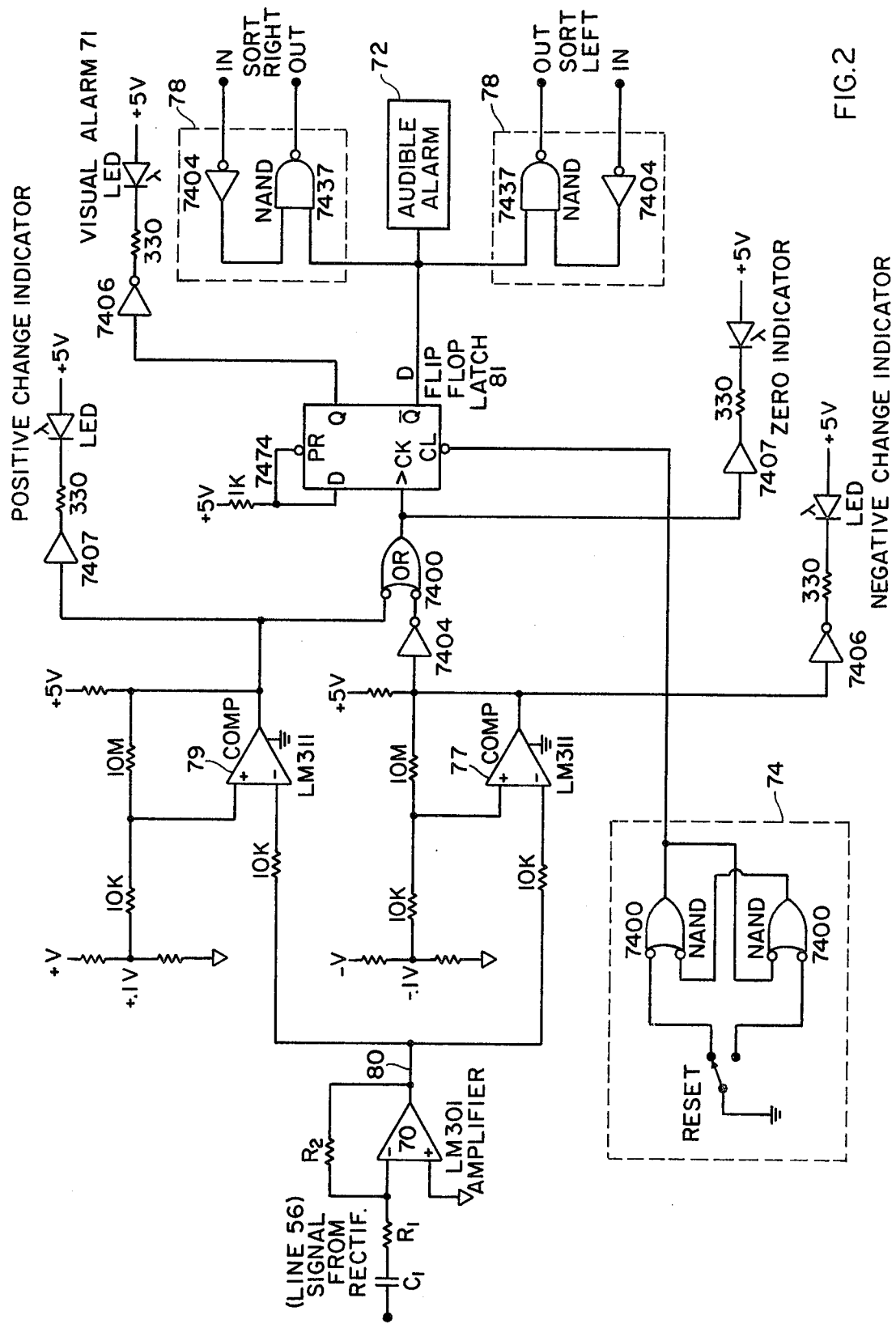
FIG. 2 shows the electrical circuitry of the fast change detector, the relay driver latching mechanism and the alarm circuits of the diagram of FIG. 1.

FIG. 2 diagramatically illustrates one form which the electrical circuitry of the fast change detector 70 may take, including the relay driving mechanism and the operator reset and the alarm. FIG. 2 shows both the audible alarm 72 and a visual alarm 71. The change of the signal on lead 56 is coupled to the amplifier 70 by capacitor C1. This A.C. signal is amplified and applied to lead 80. If the signal on lead 56 is a constant D.C. value lead 80 will be near zero potential. Lead 80 is connected to two comparators 77 and 79 which are configured to sense variations in the signal on lead 80 in either polarity away from a zero potential. A slight guard band is used to allow for amplifier offset. When the signal on lead 80 changes, the appropriate comparator senses the change and switches. The switching is sensed and latched by the latch 81. The Q output of the latch 81 switches, disabling NAND gates in 78, thus interrupting the sort signals. The switching of the latch also activates both a visual alarm 71 and an audible alarm 72. The values of capacitor $C_1$ and resistor $R_1$ are selected for speed of change while $R_1$ and $R_2$ are selected for sensitivity to change.

Figure 3:
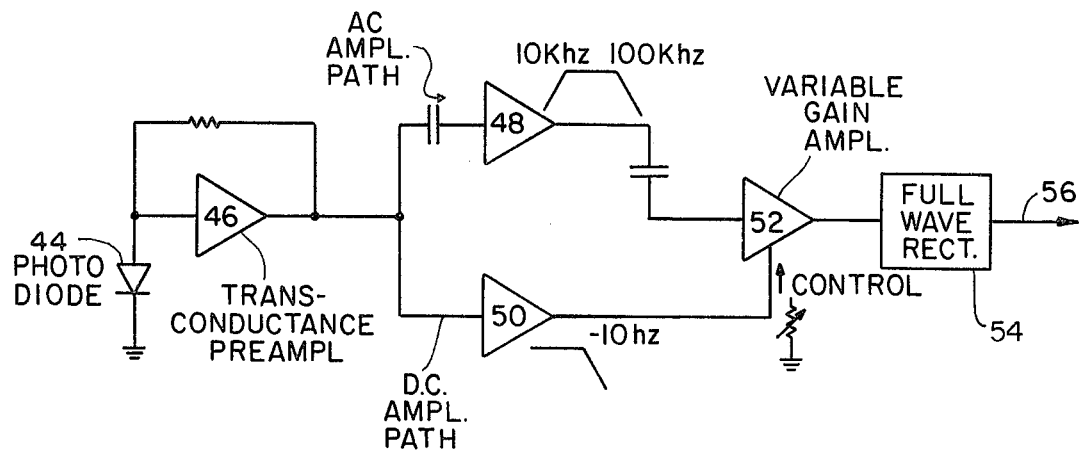
FIG. 3 shows diagrammatically the electrical circuitry for converting the signal obtained from the photo diode to a rectified D.C. which is proportional to the modulation of the light rays by the surface undulations on the jet stream.
Figure 4:
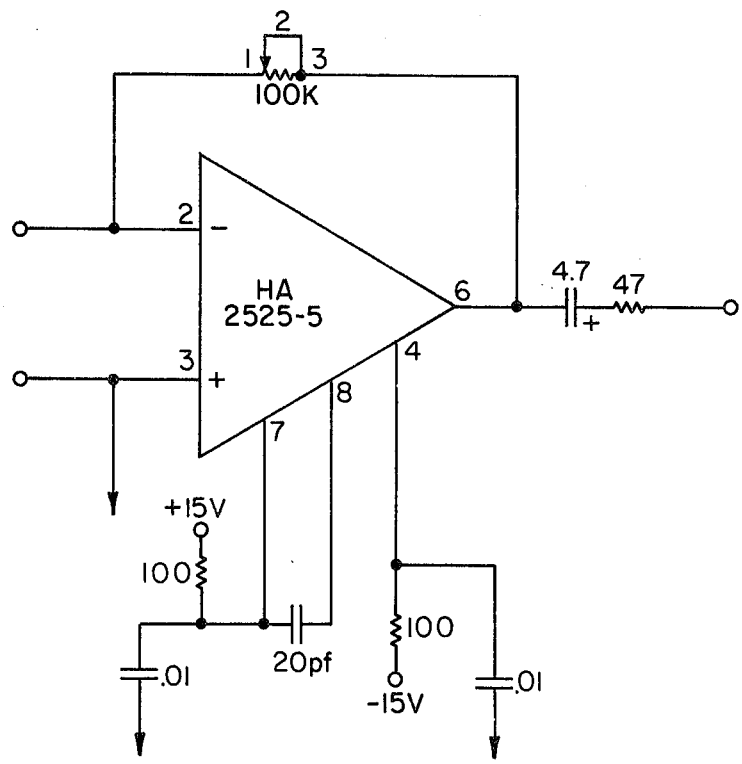
FIGS. 4 to 8 illustrate in more detail the electrical circuitry of the blocks shown in FIG. 3.
Figure 5:
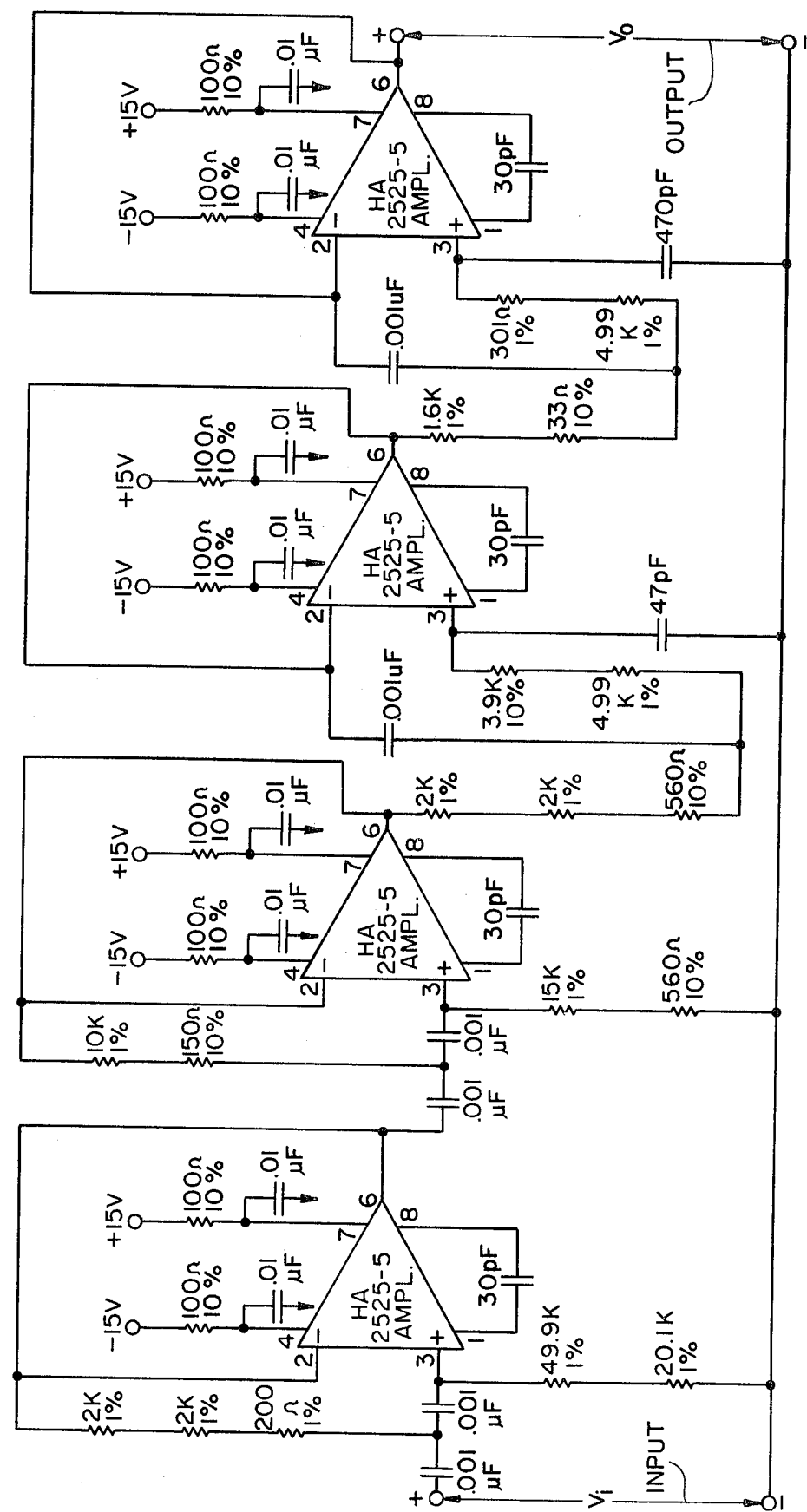
Figure 6:
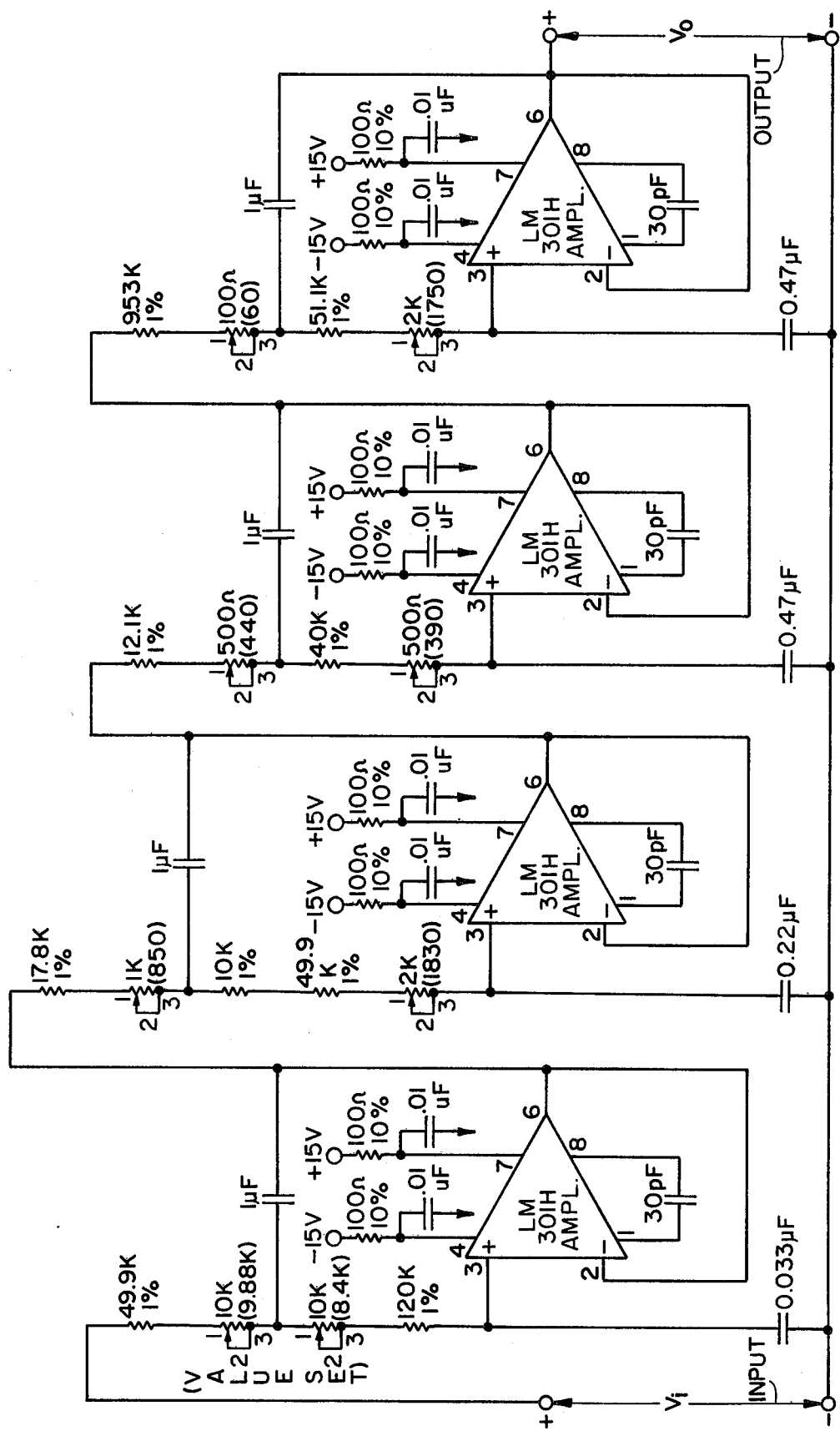

FIG. 4 illustrates the circuitry of the transimpedance pre-amplifier 46 of FIGS. 2 and 3. FIG. 5 illustrates the circuitry of the A.C. amplifier 48 of FIGS. 2 and 3. FIG. 6 illustrates the circuitry of the D.C. amplifier 50 of FIGS. 2 and 3. FIG. 7 illustrates the circuitry of the voltage controlled gain amplifier 52 of FIGS. 2 and 3. FIG. 8 illustrates the circuitry of the full wave rectifier 58 of FIGS. 2 and 3.

Although, as previously indicated, the photodiode 44 and its associated light source 20 can be moved to a point closer to the droplet breakoff point 26 where the undulations are larger, it cannot be moved to a point any closer to the breakoff point 26 which would result in the basic modulation information, the amplitude of the undulation of the jet stream 16, being lost; that is any point on the jet stream 16 beyond which would result in the output signal from the diode 44 no longer being proportional to the amplitude of the undulations on the jet stream 16. The portion of the jet stream 16 wherein such amplitude information is lost is referred to as the breakpoint region and all that portion of the jet stream 16 prior to or upstream to the actual breakoff point 26 is referred to as the uninterrupted portion of the jet stream 16.

The values of the components as well as the component parts illustrated in FIGS. 2 and 8 inclusive are merely illustrative and may be replaced by equivalent parts and circuitry to achieve the desired results.

Modifications can be made in the system of the invention without departing from the spirit and scope thereof. For example, since the A.C. path 48 contains the basic information constituting the amplitude of undulations on the jet stream, the D.C. path 50 need not be used in a simplified form of an embodiment of the invention.

What is claimed is:

1. In an apparatus for analyzing and sorting particles suspended in a liquid wherein a liquid jet stream is produced and vibrations applied thereto in order to produce undulations on the surface of said stream and subsequent breakup of the jet stream into droplets which are collected downstream, the method which comprises sensing the amplitude of undulation on the surface of an uninterrupted portion of said jet stream by radiation which is scattered by said stream during its analyzing and/or sorting mode at a fixed point on said stream prior to the breakpoint region of said stream and automatically controlling the intensity of the vibrations applied to said stream in response to a change in said amplitude of undulation at said fixed point in such direction as to restore said amplitude of undulation at said fixed point to its original state, to thereby prevent drift in said breakup point.

2. In an apparatus for analyzing and sorting particles, the method of claim 1, which includes automatically restoring the value of said amplitude of undulation at said fixed point for deviations below a predetermined level, and automatically disabling said system when the deviations in amplitude of undulation at said fixed point exceed said level.

3. In the apparatus of claim 2, the method of which includes the step of simultaneously creating an alarm when said system is disabled.

4. In an apparatus for analyzing and sorting minute particles on the basis of preselected characteristics or combinations of preselected characteristics wherein a fluid suspension in the form of a jet stream is produced and vibrations applied thereto to produce undulations on the surface of said stream and subsequent breakup of the jet stream into droplets, the method which comprises interrogating said stream by applying a concentrated beam of rays to an uninterrupted portion of said jet stream by radiation which is scattered by said stream during its analyzing and/or sorting mode at any fixed point on said stream prior to the breakpoint region, deriving a d.c. signal from said interrogation which is proportional to the amplitude of the undulations at said fixed point, and controlling the intensity of said vibrations by said d.c. signal in response to a deviation of said amplitude from a predetermined level.

5. The method of claim 4 which includes converting said signal to a visual indication as to the position on said stream of the droplet breakup point.

6. The method of claim 4 which includes utilizing said d.c. signal to disable said apparatus upon a deviation of said amplitude from a predetermined level.

7. Apparatus for analyzing and sorting minute particles while the particles are suspended in a liquid, comprising in combination: first means for producing a jet stream from said liquid suspension, second means for vibrating said jet stream to produce undulations on the surface of said stream and subsequent breakup of the stream into droplets for collection downstream, third means for impinging a beam of concentrated rays upon an uninterrupted portion of said jet stream during its analyzing and/or sorting mode at a fixed location thereon prior to the breakpoint region, a photo diode means operating in the current mode so positioned as to receive and detect the rays scattered by said jet stream as a result of impingement by said beam, rectifier means having an input and output, said input of said rectifier means coupled to the output of said photo diode means, for producing a voltage which is proportional to the amplitude of the undulations on the jet stream at said fixed location and said output of said rectifier means coupled to said second means, indicating means coupled to the output of said rectifier means and responsive to the rectified output thereof for indicating a change in the amplitude of undulation at said fixed location, and particle sensing means operating at a point prior to the breakoff point.

8. Apparatus according to claim 7, wherein said indicating means includes a meter.

9. Apparatus according to claim 7, wherein said indicating means includes an audible alarm.

10. Apparatus according to claim 7, wherein said second means includes a piezo-electric vibrator, said beam is a laser beam, said rectifier means includes a full wave rectifier, and said photo diode means is located generally in the same plane as the laser beam and also in the plane of light scattered produced by the impingement of said laser beam on said jet stream.

11. Apparatus according to claim 7 including disabling means coupled to the output of said rectifier means, said disabling means including a relay driver latching device coupled to the output of a fast change detector for disabling the sorting function of said apparatus.

12. Apparatus according to claim 7, including an automatic gain control circuit having an input coupled to the output of said rectifier means and having an output coupled to said vibrating means for altering the intensity of vibrations applied to said jet stream in response to a change in the level of said amplitude of undulation of said fixed location in such direction as to restore said amplitude of undulation at said fixed location to its original state and thereby correct for a change in the breakoff point of said jet stream.

13. Apparatus for analyzing and sorting minute particles while the particles are suspended in a liquid, comprising in combination: first means for producing a jet stream from said liquid suspension; second means for vibrating said jet stream to produce undulations on the surface of said stream and subsequent break-up of the stream into droplets for collection downstream; third means for impinging a beam of concentrated rays upon an uninterrupted portion of said jet stream during its analyzing and/or sorting mode at a fixed location thereon prior to the breakpoint region, means positioned to receive and detect rays scattered by said jet stream as a result of impingement by said beam, a trans-impedance operational pre-amplifier coupled to said last means, an A.C. path including an A.C. amplifier coupled to the output of said pre-amplifier, a rectifier means having an input and output, said input of said rectifier means coupled to the output of said A.C. amplifier, for rectifying the signal obtained therefrom and said output of said rectifier means coupled to said second means, and means coupled to and responsive to the output of said rectifier means for alerting the operator of a change in said breakoff point.

14. In an apparatus for analyzing and sorting particles suspended in a liquid, said apparatus including first means for producing a jet stream from said liquid suspension, second means for vibrating said jet stream to produce undulations on the surface of said stream and subsequent breakup of said stream into droplets for collection downstream, the improvement comprising:
third means for impinging a beam of radiation upon an uninterrupted portion of said jet stream during its analyzing and/or sorting mode at a fixed location thereon prior to the breakpoint region,
fourth means, coupled to said second means, for receiving and detecting the radiation from said third means which is scattered by said stream and for providing an output which is proportional to the amplitude of undulation at said fixed location,
fifth means electrically coupled to said fourth means for providing a signal indicating a change in the amplitude of undulation at said fixed location;
whereby said change in the amplitude of undulation correlates to a change in position of the breakoff point of said droplets.

15. Apparatus for analyzing and sorting minute particles while the particles are suspended in a liquid, comprising in combination: first means for producing a jet stream from said liquid suspension, second means for vibrating said jet stream to produce undulations on the surface of said stream and subsequent breakup of the stream into droplets for collection downstream, third means for impinging a beam of concentrated rays upon said jet stream at a fixed location thereon prior to the breakoff point of said droplets, a photo diode so positioned as to receive and detect the rays scattered by said jet stream as a result of impingement by said beam, rectifier means coupled to the output of said photo diode for producing a voltage which is proportional to the amplitude of the undulations on the jet stream at said fixed location, means coupled to the output of said rectifier and responsive to the recitified output thereof for indicating a change in the amplitude of undulation at said fixed location, an automatic gain control circuit having an input coupled to the output of said rectifier means and having an output coupled to said vibrating means for altering the intensity of vibrations applied to said jet stream in response to a change in the level of said amplitude of undulation at said fixed location in such direction as to restore said amplitude of undulation at said fixed location to its original state and thereby correct for a change in the breakoff point of said jet stream, and means coupled and responsive to the output of said rectifier means for disabling the sorting function of said apparatus, said disabling means including a fast change detector and a relay driver latching device coupled to the output of said detector.

16. Apparatus according to claim 15, including a manually controllable by-pass path for short-circuiting the output of said automatic gain control circuit.

17. Apparatus for analyzing and sorting minute particles while the particles are suspended in a liquid, comprising in combination: first means for producing a jet stream from said liquid suspension, second means for vibrating said jet stream to produce undulations on the surface of said stream and subsequent break-up of the stream into droplets for collection downstream, third means for impinging a beam of concentrated rays upon said jet stream at a fixed location thereon prior to the breakoff point of said droplets, means positioned to receive and detect rays scattered by said jet stream as a result of impingement by said beam, a trans-impedance operational pre-amplifier coupled to said last means, an A.C. path including an A.C. amplifier coupled to the output of said pre-amplifier, a rectifier coupled to the output of said A.C. amplifier for rectifying the signal obtained therefrom, means coupled to and responsive to the output of said rectifier for alerting the operator of a change in said breakoff point, a D.C. path having a D.C. amplifier also coupled to the output of said pre-amplifier, a voltage-controlled gain amplifier coupled to the outputs of both said A.C. and D.C. amplifier in such manner that the output from the D.C. amplifier controls the gain of said voltage-controlled gain amplifier, and a connection from said rectifier to said last amplifier, whereby said rectifier rectifies the A.C. signal obtained therefrom and produces a voltage which is proportional to the amplitude of the undulations on the jet stream at said fixed location.

18. In an apparatus for analyzing and sorting particles suspended in a liquid, said apparatus including first means for producing a jet stream from said liquid suspension, second means for vibrating said jet stream to produce undulations on the surface of said stream and subsequent breakup of said stream into droplets for collection downstream, the improvement comprising:

radiation means for impinging a beam of radiation upon an uninterrupted portion of said jet stream during its analyzing and/or sorting mode at a fixed location thereon prior to the breakpoint region, and sensing means, coupled to said second means, responsive to radiation from said radiation means which is scattered by said stream, for providing an output to said second means which is proportional to the amplitude of undulation at said location.

19. The apparatus according to claim 18, further including particle sensing means, responsive to said beam of radiation which illuminates said particles in said jet stream, for sensing said particles at said fixed location.

20. In an apparatus for analyzing and sorting particles suspended in a liquid wherein a liquid jet stream is produced and vibrations applied thereto in order to produce undulations on the surface of said stream and subsequent breakup of the jet stream into droplets which are collected downstream, the method which comprises sensing the amplitude of undulation on the surface of an uninterrupted portion of said jet stream by radiation which is scattered by said stream during its analyzing and/or sorting mode at a fixed point on said stream prior to the breakpoint region, and controlling said vibrations in proportion to the amplitude of the undulation at said fixed point.

* * * * *